United States Patent [19]

Casali et al.

[11] Patent Number: 5,333,622
[45] Date of Patent: * Aug. 2, 1994

[54] EARPLUG AND HEARING DEVICES FORMED IN-SITU

[75] Inventors: John G. Casali, Blacksburg; Daniel W. Mauney, Richmond, both of Va.

[73] Assignee: The Center for Innovative Technology, Herndon, Va.

[*] Notice: The portion of the term of this patent subsequent to Jul. 21, 2009 has been disclaimed.

[21] Appl. No.: 916,220

[22] Filed: Jul. 17, 1992

Related U.S. Application Data

[63] Continuation-in-part of Ser. No. 569,812, Aug. 20, 1990, Pat. No. 5,131,411.

[51] Int. Cl.⁵ .............................................. A61F 11/00
[52] U.S. Cl. ...................................... 128/864; 128/865
[58] Field of Search ........................... 128/864–868; 264/222, 466

[56] References Cited

U.S. PATENT DOCUMENTS

| | | | |
|---|---|---|---|
| 1,753,817 | 4/1930 | Aber | 128/864 |
| 2,967,913 | 1/1961 | Aubert | 128/864 |
| 3,041,856 | 7/1962 | Neal | 128/864 |
| 3,097,059 | 7/1963 | Hoffman | 128/864 |
| 3,344,220 | 9/1967 | Cook | 128/864 |
| 3,440,314 | 4/1969 | Frisch | 128/864 |
| 3,696,090 | 10/1972 | Lampe | 128/864 |
| 3,897,376 | 7/1975 | Lampe | 128/864 |
| 4,459,247 | 7/1984 | Rothemund | 128/864 |
| 5,131,411 | 7/1992 | Casali | 128/864 |

*Primary Examiner*—Michael A. Brown
*Attorney, Agent, or Firm*—Whitham, Curtis & Whitham

[57] ABSTRACT

A custom-molded earplug (18) for swimming protection, hearing protection, and the like, is fabricated in situ by depositing a foaming material (14 or 24) within a person's ear (10 or 42) and allowing the foaming material to form foam (16 or 44). Acoustic and electronic equipment such as a Helmholtz resonator or other tuned device capable of modifying sound waves, a communications transmitter, a communications receiver, a communications transceiver, a hearing aid, an ear microphone, a personal earphone, and a hearing test transducer or probe tube can be fabricated in the ear in a similar fashion. Temperature sensing elements may also be incorporated within or positioned by the foaming material to provide an in the ear thermometer.

8 Claims, 3 Drawing Sheets

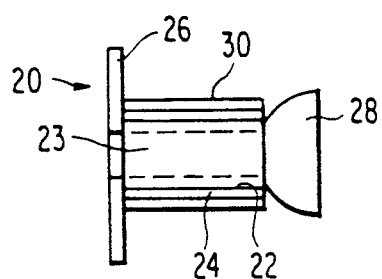
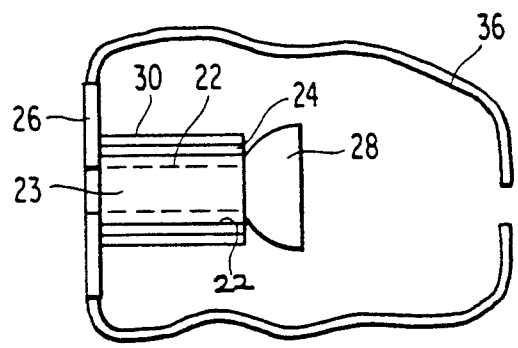
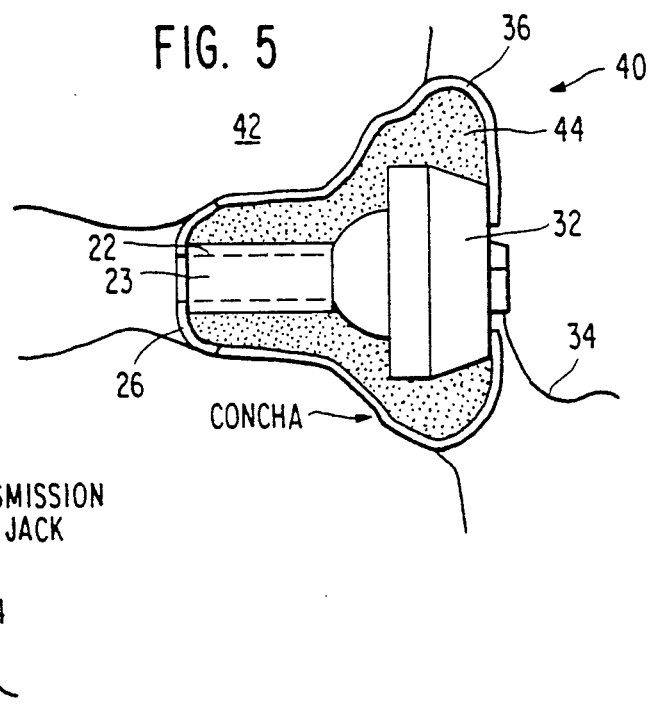

5,333,622

EARPLUG AND HEARING DEVICES FORMED IN-SITU

CROSS-REFERENCE TO RELATED APPLICATION

This patent application is a continuation-in-part application of the co-pending U.S. patent application having Ser. No. 07/569,812 filed Aug. 20, 1990, now U.S. Pat. No. 5,131,411, and the contents of the patent are hereby incorporated in this patent application.

BACKGROUND OF THE INVENTION

1. Field of the Invention

The present invention generally relates to custom-fitting earplugs that are formed in situ and, more particularly, to a device and method for creating a custom-fitting earplug in the ear of the prospective user which utilizes a foaming agent that expands and fills the ear canal after its insertion in the patient's ear. These earplugs have multiple applications, including: noise suppression, ear seals for swimming and sleeping, ear canal measurement devices and casts for ear plugs and hearing aids. Furthermore, these earplugs are useful in the creation of acoustic and electronic ear devices, including: communications receiver, transmitter, and transceivers, hearing aids, hearing test transducer or probe tube, ear microphones, personal earphones (miniature loudspeaker), tuned resonating devices for sound wave modification, and other acoustic and electronic devices.

2. Description of the Prior Art

Earplugs are presently in common use in a number of activities. Airport and heavy industry personnel typically use noise-attenuating earplugs on a daily basis to prevent hearing damage. The Occupational Health and Safety Administration (OSHA) presently requires that all workers exposed to noise of 85 decibels A-weighted (dBA) time-weighted average over an eight hour day must be supplied with hearing protectors. According to recent estimates of the Environmental Protection Administration (EPA), over nine million American workers are exposed to levels above the threshold levels set by OSHA on a daily basis. In addition to industry, people often use earplugs when operating light machinery such as chain saws, when participating in sporting activities such as swimming and shooting, and when attending various spectator events such as automobile races, truck pulls, and rock concerts.

Prior art "universal fit" type earplugs typically comprise a foam, mineral fiber, wax, or putty-like (e.g., Swedish Wool) material which is either unencapsulated or sheathed in a thin, smooth outer skin. Outside the wearer's ear the plugs may have a cylindrical or other pre-formed shape. These plugs are often termed "universal fit" because they are intended to adapt to the contours of any person's ear canal to provide hearing protection. To install the "universal fit" earplug, the wearer must first compress and/or form the plug by kneading, wadding or rolling it up and then position the plug in his or her ear canal. In the case of the foam earplug, the plug must be inserted before it expands. After insertion, the "universal fit" plug is supposed to assume the natural contours of the ear canal by expansion therein. Typical examples of "universal fit" foam earplugs are shown and discussed in U.S. Pat. No. 4,160,449 to Wade, U.S. Pat. No. 4,459,247 to Rothemund, and U.S. Pat. No. 4,434,794 to Leight.

Universal fit earplugs suffer from a variety of problems. First, the plugs are difficult for many individuals to insert properly. If the plug is incorrectly formed by the user as it is inserted in the ear canal, wrinkles and voids may develop that allow sound leakage to the user's eardrum, thereby reducing the protective effectiveness of the plugs to the wearer. Second, some of the plugs typically are larger than people may need because the commercial vendor has designed the plugs to fit ear canals that are larger than average in hopes of accommodating a wide range of users. Third, some users find universal fit earplugs to be uncomfortable.

Custom-molded earplugs can be an attractive alternative to universal fit earplugs and have advantages in their comfort, more reliable fit, and lower long-term costs due to longer usable life. Also, custom-molded earplugs may offer certain hygiene advantages in dirty environments since the user does not have to compress or form them with their fingers prior to insertion. Custom-molded earplugs are essentially a mold of the wearer's ear canal and concha of the outer ear. Hence, the earplugs can be precisely positioned in the ear by the wearer so that his or her ear canal is not subjected to undue pressure when the plugs are installed and because of the personalized fit, sound is effectively blocked by the plugs. Some custom-molded earplugs are made by making a positive casting of the ear canal first, then making a negative mold, and finally making the earplug from the negative mold.

U.S. Pat. No. 3,097,059 to Hoffman discloses a method of making earplugs in situ which eliminates the need for making negative and positive casts. The earplug is fabricated by depositing a mass of acrylic resin in the wearer's ear and allowing the acrylic to cure therein. U.S. Pat. Nos. 3,696,090, 3,782,379, 3,897,376, and 3,925,277 to Lampe disclose two part room temperature vulcanizable rubber compositions which are used to form earplugs in situ in a manner similar to that described in Hoffman.

Casting an earplug in situ using a self-curing resin is not an ideal method for creating a custom-molded earplug. A doctor or a trained technician will be required to make the mold since the mold's manufacture requires a highly viscous resin or putty to be deposited deep in the patient's ear. The objective when taking the earmold is to obtain an impression which follows all inner contours of the ear canal and which has no voids or creases due to the trapped air pockets. Packing the resin in the ear canal to meet this objective can be very painful to the patient. During packing, air is trapped between the tympanic membrane (eardrum) and the viscous resin. Because of the viscosity of the resin, air cannot easily escape the ear canal through or around the resin; therefore, external pressures exerted to pack the resin in the ear will be transferred to the tympanic membrane and to middle ear structures. The viscous resin can be forced into the ear canal using a large syringe. Alternatively, a paste-like resin material can be inserted into the ear canal using a putty knife or the doctor's thumb to force the resin down into the ear canal. After the resin is added to the ear, it may be necessary to manually apply some pressure from outside the ear to assure that the resin hardens within the canal. The patient must sit motionless, without jaw movement, for several minutes until the mold solidifies.

Besides severe pain being caused to many patients, casting an earplug in situ also suffers from the common problem of voids being formed therein which reduce the effectiveness of the final earplug produced. This results in the need for taking multiple impressions. For example, if the resin is not packed into the user's ear tightly enough, air pockets will be created in spaces where the resin does not contact the walls of the ear canal or invisible voids may occur within the resin structure itself. British Patent 2,084,072 to Carr addresses this problem by providing additional coatings on the outside surface of the plug until a perfect impression is made. Such a tedious process for forming an earplug is not acceptable.

British Patent 2,090,535 to Fekry discloses an improved method for creating an earplug in situ. A water swellable insert is first installed in the ear, then water drops are added to the insert causing it to expand inside the ear to a preset shape. While the insert described in the patent may avoid the disadvantage of pain to the wearer of custom-molding earplugs (assuming the preset size does not exert pressure on the ear canal walls), it does not create a custom-fitting earplug in its expanded state. Rather, the insert expands to one preset shape and would suffer from the same disadvantages discussed above in conjunction with universal fit type earplugs.

French patent 1,559,694 to Avot discloses an earplug which comprises a deformable capsular enclosure containing liquid precursor components separated by a partitioning element. Finger pressure brings the two liquids separated by the partition together to create a foam which expands within the ear. The Avot earplug suffers from the problem that it has no structural rigidity and will tend to wad up on initial insertion if it is extracted and re-installed in the ear. Furthermore, being a liquid state prior to initial insertion which will determine its initial formation, and having no structural rigidity, the earplug capsule will not be insertable deep enough into the ear canal to obtain an accurate impression.

SUMMARY OF THE INVENTION

It is therefore an object of this invention to provide an earplug device which can form a custom-fitting earplug in situ with a minimum of pain and discomfort to the patient.

It is another object of the invention to provide an earplug device which can form a custom-fitting earplug in situ without complex molding operations and without requiring special medical or audiological skills.

It is another object of the invention to enable production of a custom-fit earplug in-situ which is immediately usable and does not require positive casts and negative molds nor waiting on the part of the patient.

It is still another object of the invention to provide a device which can form in-situ a custom-fitting hearing aid, ear microphone, personal earphone (miniature loudspeaker), communications transmitter, receiver or transceiver, hearing test transducer or probe tube, or other electronic device.

It is still another object of the invention to provide a device which can form in-situ a custom-fitting acoustic device such as a Helmholtz resonator or other tuned resonator device which can modify sound waves.

It is yet another object of the invention to provide an earplug forming device which can create in-situ a custom-fitting earplug which holds, positions or has an embedded thermistor or thermometer or like element which can be used to monitor the core temperature of the wearer.

It is yet another object of the invention to provide a device which can form a mold of the ear canal in situ which can be used for selecting pre-sized earplugs or as a cast for creating a mold for earplugs or hearing aids.

It is an additional object of this invention to provide a means of obtaining anthropometric ear canal measurements.

It is a further object of this invention to provide a custom-fitting earplug which can act as a hearing protector to guard against high noise environments or seal out water for a swimmer.

According to the invention, a foaming material is positioned within the ear canal of the prospective wearer and is used to create a custom-fitting earplug. The foaming material, in its unexpanded state, is small in size and may be, though not necessarily, surrounded by a thin plastic or membrane material which constitutes a sheath. This device comprises a core approximately 0.5–2.5 cm long coated with a foaming material which is protected by a removable wrapping and terminated by a protective flange. Further, the device includes a removable keeper, stem, and an optional inserter to aid in the donning and doffing of the device. After the device has been placed in the ear, the foaming material expands to create a foam which fills the ear canal and part of the concha. Preferably, ambient conditions within the ear, such as heat and humidity, trigger the foaming action. Other external agents, such as water or chemical products can also be used to induce foaming on demand. During foaming, the wearer should apply only slight fingertip pressure to the earplug so that the foaming action does not push the device out of the ear. After the foam has formed and is set, the earplug can be removed and re-installed whenever the wearer desires. The sheath provides a smooth, cleanable exterior surface for the earplug which has been created in situ, as well as defines and limits the area into which the foam can expand.

The custom-fitting earplug created as described above may also simply serve as a cast for the fabrication of a mold for other custom-fitting earplugs or as a model against which pre-formed earplugs might be selected. This would allow the use of foaming materials which that need not have the sound protection or water repellant properties of the final device.

In a further embodiment of the invention, a device containing the foaming material is used to create an ear coupler mounting for a custom-fitting hearing aid or similar device. The device comprises a small diameter (approximately 1–3 mm) cylindrical body member of approximately 0.5–2.5 cm having a hollow passage therethrough. A protective flange and a mounting flange are positioned on opposite ends of the body member. The mounting flange is positioned above the hollow passage in the cylindrical body member and is modifiable to secure ear microphones, hearing aids, personal earphones, communications transmitters, receivers or transceivers, hearing test transducers or probes or other electronic equipment. In addition, acoustic equipment such as Helmholtz resonators and other tuned resonating devices could be connected to the mounting flange. Carried on the outside surface of the cylindrical body member is a foaming material. The foaming material can be kept in a stable, non-reactive state by applying a tape material over top. A membrane sheath can be secured to the protective flange of the cylindrical body and extend over the outside of the entire device. To create a custom-fitting hearing aid, ear microphone, communications transceiver, transmitter, or receiver, etc., packaged electronics are connected to the mounting flange of the device, the tape is removed from over top the foaming material, and the combined device is placed in the patient's ear canal. The foaming material is then induced to expand to fill the spaces between the cylindrical body member and the ear canal with a foam material. After the foam has formed and set, the hearing aid or ear microphone can be removed and re-installed in the patient's ear whenever desired. The hollow passage in the cylindrical body allows auditory communication directly between the patient's eardrum and the hearing aid or ear microphone. Alternatively, wiring from the electronics to a transducer near the eardrum may pass through the foam of the earplug.

It is noted that a modification to this further embodiment would have the packaged electronics embedded in the foam material, rather than positioned on a mounting flange of a hollow body member. In this case, all that would be required would be a package that provides acoustic and/or electronic access to the packaged transmitting and/or receiving electronics, and the foaming material in a non-foamed state. This modification could also be employed with acoustic elements such as Helmholtz resonators.

Furthermore, the earplugs created by this technique are ideal for the creation of a custom-fitting temperature measurement device. Specifically, a temperature sensitive device (thermometer, thermistor, etc.) is mounted inside the package containing the foaming material in its non-foamed state. The wiring extends out of the package. If the mounting arrangement for packaged electronics is used, the wiring may pass through the core of the earplug. After the earplug is formed in-situ, there is a tight seal formed with the ear canal. This sealed arrangement allows for highly accurate core temperature measurements of the individual to be made, without contamination by ambient conditions outside the ear.

BRIEF DESCRIPTION OF THE DRAWINGS

The foregoing and other objects, aspects and advantages will be better understood from the following detailed description of a preferred embodiment of the invention with reference to the drawings, in which:

FIG. 2 is a cross-sectional side view of a package used in creating a custom-fitting hearing aid;

FIG. 3 is a cross-sectional side view of the package shown in FIG. 2 where a sheath material has been connected to the rear protective flange of the package;

FIG. 4 is a representational side view of a ear microphone and transmission wire;

FIG. 5 is a cross-sectional side view of a custom-fitting ear microphone created with the device shown in FIG. 3.

DETAILED DESCRIPTION OF THE PREFERRED EMBODIMENTS OF THE INVENTION

Figure 1A:
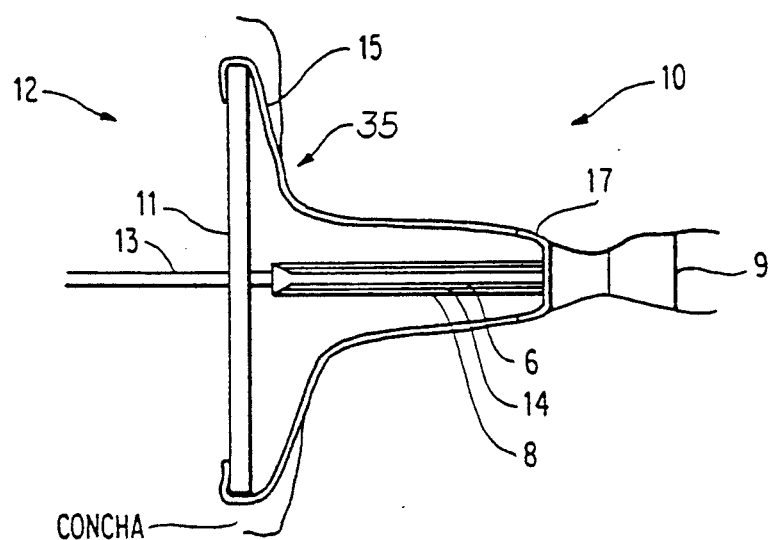
FIGS. 1a and 1b are cross-sectional side views of a person's ear canal before and after creation of a custom-fitting earplug, respectively.
Figure 1B:
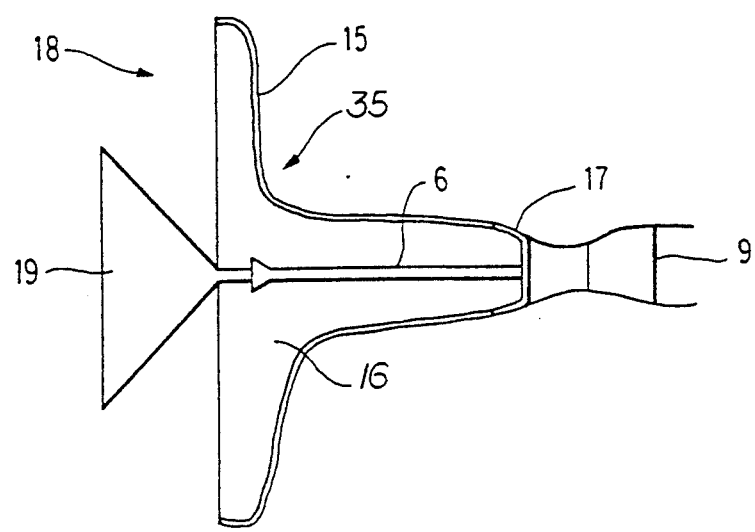

Referring now to the drawings, and more particularly to FIGS. 1a-b, there is shown generally the ear 10 of a person with a package 12 positioned within the person's ear canal. The package 12 contains a foaming material 14 coated on a core or body member 6 and an outer sheath 15. The foaming material 14 is preferably chosen to expand to form a foam 16 under the ambient conditions present within the ear 10, such as body temperature and humidity. However, it is anticipated that other triggering mechanisms, such as adding a chemical, exposure to ultraviolet light, water, or any other convenient treatment of the foaming material 14 could be used to activate the foaming material just prior to insertion in the ear 10. Selection of the foaming material 14 may control the type of triggering mechanism used. In addition, the quantity of foaming material 14 used will be dependent on type of foam 16 and the anthropometry of the ear canal, and should be selected so that the foam 16 will slightly overfill the volume in the ear canal and slightly protrude out into the concha of the ear 10. It is also preferred that the foaming material 14 and foam 16 created during expansion be non-inflammatory, dielectric, and retain its final expanded shape and size conforming to the ear canal walls. However, it should be understood that in certain applications, such as in the creation of an ear mold which is used to make other custom-fitting earplugs, the foam material may not need to be non-inflammatory. Likewise, it may not always be necessary for the foam to retain its final expanded shape. For example, with disposable earplugs, designed for one time use only, shape retention would not be required. Also, in an earplug configuration suitable for thermal measurements, shape retention may not be necessary. The foam 16 should also act as a barrier by reflecting and by attenuating sound, and have a high transmission loss. To achieve a high transmission loss, the foam 16 should generally have a high flow resistance, a high density, and a moderately low bulk modulus.

In operation, a person places the package 12 in his or her ear 10 using stem 13 and keeper 11. Because of the ambient conditions or the addition of triggering agents applied just prior to insertion, the foaming material 14 expands to fill the ear canal with foam 16. A removable wrapping 8 can be used to protect the foaming material 14 prior to insertion and then removed upon insertion. The stem 13 aids insertion by providing an area for the forefinger and thumb to grasp and guide package 12 into the canal. The keeper 11 prevents insertion of the device too far into the ear canal as well as to guide the overflowing foam into the contours of the concha. The stem 13 and keeper 11 are not necessarily present during the wearing of the earplug. Preferably, the stem 13 and keeper 11 can be easily removed from the earplug through a twisting motion once the foaming has taken place. The twisting motion can serve to detach the stem 13 from a fitting connecting it to the core 6 or it could serve to physically break off the stem 13 at a weakened section. The optional inserter 19 can then be affixed to the earplug through a twisting motion and serve to aid in the donning and doffing of the device under normal operating conditions.

An "eardam" 9, made of a cotton or mineral fiber swab attached to a thread extending out of the ear, may be optionally inserted ahead of the package 12, to ensure that the foam 16 does not reach the eardrum. However, the built-in protective flange 17 on the insertion end of the package is intended for this purpose and may render eardams unnecessary. Preferably, the protective flange 17 is a soft, flexible polymer material which bends backwards into a hemispherical shape when inserted so as to prevent undue irritation to the ear canal and to limit the forward (toward eardrum) expansion of the foam 16. The protective flange 17 should be no more than 15 mm in diameter.

In order to keep the package 12 within the ear 10 during foaming, the person simply holds his or her thumb and/or forefinger against the stem 13 or keeper 11. After the foam 16 has set, a custom-fitting earplug 18 will have been created. The earplug 18 can then be removed and re-installed in the ear 16 whenever desired. Depending on the choice of foam, the earplug 18 retains its shape upon removal from the ear 10. The optional outer sheath 15 of the package 12 gives a smooth, cleanable surface to the earplug 18 produced. The sheath 15, in conjunction with the protective flange 17, can serve to distance the person's eardrum (not shown) from the foam 16. Hence, the need for installing an eardam in the ear 10 before creating the earplug 18 is eliminated.

A particular advantage of the above device and method of making earplugs in situ is that the earplug 18 is created and used with relatively little pain and discomfort to the wearer. The ear canal is merely subjected to the expansion pressure of the foam 16 as it expands, and this is controllable through foam selection.

Because the device and method of making earplugs is relatively rapid and painless and fills the wearer's ear canal, the device could be used as a tool for measuring and determining the shape of the wearer's ear canal. After making the earplug 18, it can be extracted and any portion can be quickly measured with available measuring gauges. Hence, population data on the anthropometry of ear canals can be rapidly gathered. Prior art anthropometric data has been achieved through the tedious and relatively imprecise process of inserting spherical balls of fixed sizes in the patient's ear. In addition, the earplug 18 could be used in such applications as forming a casting mold to make custom-fitting earplugs from other materials, or it could be used for selecting among different sizes of pre-molded earplugs which would best fit the individual. Hence, the invention also contemplates making earplugs 18 out of a foam that may not necessarily meet the needs of the particular application. For example, if the earplug 18 served as a mold for making other earplugs or in selecting among premolded earplugs, rather than as a the protective device itself, the foam chosen need not be water protective or have sound reducing properties, etc.

FIGS. 2-6 disclose further embodiments of this invention wherein a custom-fitting electronic, acoustic, and temperature measuring equipment could be packaged in an earplug device which utilizes in situ formation of a foam to seal against the contours of the ear canal.

FIG. 2 shows a device 20 comprised of a cylindrical body 22 having a foaming material 24 carried on its outer surface. The cylindrical body 22 has a central bore 23 therethrough and includes a protective flange 26 on one end and a mounting flange 28 on its other end. The cylindrical body 22, protective flange 26, and mounting flange 28 could be integrally molded or could be assembled from three separate pieces. The protective flange 26 can serve to protect the person's eardrum (not shown) from the foam 16. The protective flange 26 would serve the same purposes described above in conjunction with FIGS. 1a and 1b. The mounting flange 28 should be sturdy and rigid enough to support a packaged electronic component (shown in FIG. 4 as item 32) and serves to join the component to the cylindrical body 22 at the central bore 23 so that airborne sound waves pass relatively unobstructed therethrough to the person's eardrum.

The packaged electronic component 32 can be a communications receiver, transmitter or transceiver such as those sold by Maxon ®, an ear microphone or personal earphone such as the AICOMM AIMic, a hearing aid, a hearing transducer or probe tube, or any other desired component. In addition to electronic components, acoustic devices such as a Helmholtz resonator or other tuned device to modify sound waves could be used. Also, it is particularly contemplated that a non-acoustic or electro-acoustic device (e.g., transmitter or receiver) could be used. In particular, a temperature sensing device such as a thermometer, thermocouple, or thermistor could be used.

The electronic component 32 may or may not have a transmission wire 34 which can be disconnected. A removable wrapping 30 can be positioned over the foaming material 24 so that it is protected from the elements prior to use. FIG. 3 shows that an optional sheath 36 can be affixed to the protective flange 26. The sheath 36 would serve the same purposes described above in conjunction with FIGS. 1a and 1b.

As shown in FIG. 5, in-ear mount for the hearing aid, personal microphone, hearing test transducer or probe tube, communications receiver, transmitter or transceiver, or other electronic, temperature sensing, or acoustic component is fabricated in situ in the person's ear 42. The foaming material 24 (shown in FIGS. 3 and 4) expands to fill the ear canal with a foam 44 as described above. After the foam 44 has set, the device can freely be removed from and re-installed in the ear 42. In FIG. 5, the electronic component 32 is in direct audible communication with the eardrum through central bore 23.

Figure 6:
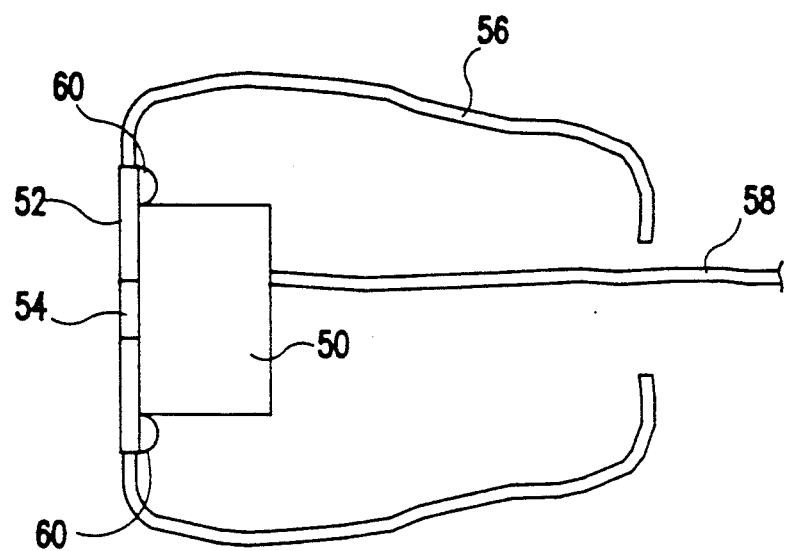
FIG. 6 is an alternative arrangement for a custom-fitting electronic component.

FIG. 6 shows an alternative configuration to FIG. 5 where a component 50 is positioned on a plastic element 52 with a bore hole 54 therein which allows access to the component 50. The plastic element 52 is preferably flexible so that it can bend on contact with the ear canal. A sheath 56 could be provided to fulfill the functions described above for sheath 36. Wires 58 could be provided for connections to the component 50. A major distinction between FIG. 6 and FIG. 5 is that the hollow, cylindrical body 22 is eliminated in FIG. 6. The component 50 could be any of the components described above for component 32 in FIG. 5. Specifically, component 50 could be communications receiver, transmitter, or transceiver, a hearing aid, a hearing test transducer or probe tube, an ear microphone, a personal earphone, or other electronic device, or it could be an acoustic device such as a Helmholtz resonator or other tuned device used to modify sound waves, or it could be a temperature sensing element such as a thermometer, thermistor, or thermocouple. It should be understood that the component 50 need not be "mounted", as is component 32 in FIG. 5. All that is required is that the foaming material in a non-foamed state be present together with the component 50 as a package which is insertable in the ear of a person. The foaming material 60 used to create the foam could be positioned on the plastic element 52 around the component 50 or in other locations. The foam which is produced could hold the component 50 in place. The component 50 could be located on either endo of the eaplug or anywhere between the two ends.

A particular application contemplated by this invention is an "in-the-ear-thermometer". In many medical or research situations such as, for example, in the management of heat stress, accurate "core temperatures" (actual body temperature rather than skin surface temperature) are required for proper treatment. In the past, these measurements were made by under the tongue thermometers and by rectal thermometer. If the component 32 in FIG. 5 or the component 50 in FIG. 6 is a temperature sensitive device (thermometer, thermistor, etc.), the foam 44 which is produced from the foaming material 14, 24, or 60 will tightly seal the ear canal and the component 50 can be used to make highly accurate core temperature readings. In operation, an earplug assembly like that shown in FIGS. 5 or 6 would be placed in the ear canal of a patient. The foam would be activated and permitted to set after it fills the ear canal. Subsequently, temperature measurements could be made. Wires 58, shown in FIG. 6, could be used to transmit the temperature signals. Alternatively, the component 50 could be battery powered, could have a radio transmitter or incorporate other telemetry means. If the arrangement in FIG. 5 is used, wiring connections could pass through the hollow core 23.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An in the ear, custom-fit, electronic device, comprising:
    a body member positionable within an ear canal of a person;
    an electronic device; and
    a foaming material in a non-foamed state carried by said body member, said foaming material in said non-foamed state being activatable to fill said ear canal with a foam material, said body member and said electronic device being positioned within said foam material after activation of said foaming material in said non-foamed state.

2. An in the ear, custom-fit, electronic device as recited in claim 1 wherein said electronic device is a tuned device capable of modifying sound waves.

3. An in the ear, custom-fit, electronic device as recited in claim 1 wherein said electronic device is selected from the group consisting of a communications transmitter, a communications receiver, a communications transceiver, a hearing aid, an ear microphone, a personal earphone, a hearing test transducer, and a probe tube.

4. An in the ear, custom-fit, electronic device as recited in claim 1 wherein said body member is a cylindrical hollow core member.

5. An in the ear, custom-fit, electronic device as recited in claim 4 further comprising a means for mounting said electronic device on said cylindrical hollow core member.

6. An in the ear, custom-fit, electronic device as recited in claim 1 wherein said body member is a plastic disk and said electronic device is positioned on said plastic disk.

7. An in the ear, custom-fit, electronic device as recited in claim 1 wherein said electronic device is a temperature sensitive element.

8. An in the ear, custom-fit, electronic device as recited in claim 7 wherein said temperature sensitive element is selected from the group consisting of a thermometer, a thermistor, and a thermocouple.

* * * * *